United States Patent [19]

Della Ciana et al.

[11] Patent Number: 6,136,612
[45] Date of Patent: Oct. 24, 2000

[54] SULFO BENZ[E]INDOCYANINE FLOURESCENT DYES

[75] Inventors: Leopoldo Della Ciana, Lugo; Andrea Grignani, Chieri; Mariacristina Cassullo, Santhia; Giuseppe Caputo, Turin, all of Italy

[73] Assignee: Sorin Biomedica Cardio S.p.A., Turin, Italy

[21] Appl. No.: 09/043,767

[22] PCT Filed: Oct. 8, 1996

[86] PCT No.: PCT/EP96/04377

§ 371 Date: May 11, 1998

§ 102(e) Date: May 11, 1998

[87] PCT Pub. No.: WO97/13810

PCT Pub. Date: Apr. 17, 1997

[30] Foreign Application Priority Data

Oct. 9, 1995 [IT] Italy .................. MI95A2049

[51] Int. Cl.[7] ............... G01N 33/533; C07D 209/56
[52] U.S. Cl. .............. 436/546; 435/6; 436/531; 436/800; 436/817; 530/391.3; 530/402; 530/408; 548/427
[58] Field of Search ............... 435/6; 548/427; 436/546, 800, 817, 531; 530/391.3, 402, 408

[56] References Cited

U.S. PATENT DOCUMENTS 5,268,486  12/1993  Waggoner et al. .................. 548/427
5,453,505   9/1995  Lee et al. .......................... 544/124

FOREIGN PATENT DOCUMENTS 0 288 076 A2  10/1988  European Pat. Off. .
0 350 026 A2   1/1990  European Pat. Off. .
0 433 466 A1   8/1991  European Pat. Off. .
0 533 302 A1   3/1993  European Pat. Off. .
0 626 427 A1  11/1994  European Pat. Off. .

*Primary Examiner*—Mary E. Ceperley
*Attorney, Agent, or Firm*—Popovich & Wiles, P.A.

[57] ABSTRACT

The present invention is directed to fluorescent dyes and its valence tautomers of the formula

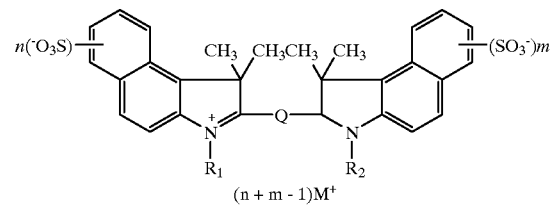

wherein Q represents a conjugated moiety that increases the fluorescent quantum yield of the compound; $R_1$ is a functionalized group of the formula—$(CH_2)_jY$, wherein Y is selected from the group consisting of $SO_3H$, COOH, $NH_2$, CHO, NCS, epoxy, phthalimido, and COOZ, wherein Z represents a leaving group; $R_2$ is a functionalized group of the formula —$(CH_2)_kY'$, wherein Y' is selected from the group consisting of $SO_3H$, COOH, $NH_2$, CHO, NCS, epoxy, phthalimido, and COOZ, wherein Z represents a leaving group; $M^+$ is a counterion selected from the group consisting of ammonium, alkali metal cations, and alkaline earth metal cations; n=1 to 4; m=1 to 4; j=2 to 10; and k=2 to 10.

22 Claims, 5 Drawing Sheets

SULFO BENZ[E]INDOCYANINE FLOURESCENT DYES

FIELD OF THE INVENTION

The present invention relates to a new class of fluorescent dyes and their valence tautomers belonging to the sulfo benz[e]indocyanine family. The instant invention also relates to the synthesis of the new class of fluorescent dyes belonging to the sulfo benz[e]indocyanine family. The new fluorescent dyes can be excited using powerful yet inexpensive light emitting diodes and diode lasers, they exhibit good water solubility, and can be attached or conjugated to a wide variety of molecules or surfaces for labeling purposes. The new fluorescent dyes are particularly useful in techniques such as immunoassays, DNA probes, high pressure liquid chromatography (HPLC), capillary electrophoresis, fluorescence polarization, total internal reflection fluorescence (T.I.R.F.), flow cytometry, DNA sequencing, and optical sensors.

BACKGROUND OF THE INVENTION

The use of fluorescence technology has become widespread in the areas of clinical chemistry, i.e., laboratory testing and the medical diagnostic areas. The technology is particularly effective for making very sensitive and specific test determinations, competing effectively in many areas with radioimmunoassays and enzymatic immunoassays.

The phenomenon of fluorescence occurs when a molecule or atom is bombarded with light of given wavelengths; namely, the conversion of that light to an emission of light of a different wavelength. In macroscopic terms, the conversion is instantaneous, but in real terms the finite time differences between the absorption of the light by the molecule and the time interval during which the emitted light is given off is a measure of the characteristics of the bodies being measured.

The process of fluorescence starts with the absorption of light photons by atoms or molecules. The frequency of light absorption varies with the atom or molecule involved.

Fluorescent molecules in any specific environment have two characteristic spectra. The first, the so-called excitation spectrum, is represented by a series of wavelengths of light which are absorbed by the molecule with differing efficiencies. That is, out of a possible number of existing wavelengths which may be absorbed by the molecule to cause fluorescence, usually one of these will be absorbed at a greater level. Most atoms or molecules that absorb light convert this light energy into heat, but a few emit light or "fluoresce" at a lower light frequency. Photon absorption occurs rapidly in about $10^{-15}$ seconds. If the light excitation is abruptly interrupted, as with a very short pulse of light, photon light emission in the second spectrum will decay rapidly with a time constant that depends on the atom or molecule involved. The range of decay times is usually between $10^{-10}$ to $10^{-6}$ seconds (0.1 to 1000 nanoseconds). The intensity of the emission spectrum is directly proportional to the intensity of the exciting light.

It happens also that the intensity of the emitted light is also directly proportional to the concentration of the fluorescent molecules in the sample. It thus can be seen that a very sensitive technique for measuring the concentration of a fluorescent body can be evolved by controlling the intensity of the exciting light and other physical constants of the measuring system.

The analytical value of fluorescence decay time measurement arises from the fact that each atom or molecule has its own distinctive rate of decay. Each atom or molecule is excited at a different frequency and emits light only at a particular emission wavelength.

Analytical probes having fluorescent labels are valuable reagents for the analysis and separation of molecules and cells. Specific applications include: (1) identification and separation of subpopulations of cells in a mixture of cells by the techniques of fluorescence flow cytometry, fluorescence-activated cell sorting, and fluorescence microscopy; (2) determination of the concentration of a substance that binds to a second species (e.g., antigen-antibody reactions) in the technique of fluorescence immunoassay; (3) localization of substances in gels and other insoluble supports by the techniques of fluorescence staining. These techniques are described by Herzenberg et al., "Cellular Immunology," 3rd ed., chapt. 22, Blackwell Scientific Publications, 1978 (fluorescence-activated cell sorting); and by Goldman, "Fluorescence Antibody Methods," Academic Press, New York, 1968 (fluorescence microscopy and fluorescence staining).

When using fluorescers for the above purposes, there are many constraints on the choice of the fluorescer. One constraint is the absorption and emission characteristics of the fluorescer. Many ligands, receptors, and materials associated with such compounds in the sample in which the compounds are found, e.g., blood, urine, and cerebrospinal fluid, will fluoresce and interfere with an accurate determination of the fluorescence of the fluorescent label. Another consideration is the ability to conjugate the fluorescer to ligands and receptors and the effect of such conjugation on the fluorescer. In many situations, conjugation to another molecule may result in a substantial change in the fluorescent characteristics of the fluorescer and in some cases, substantially destroy or reduce the quantum efficiency of the fluorescer. A third consideration is the quantum efficiency of the fluorescer. Also of concern is whether the fluorescent molecules will interact with each other when in close proximity, resulting in self-quenching. An additional concern is whether there is non-specific binding of the fluorescer to other compounds or container walls, either by themselves or in conjunction with the compound to which the fluorescer is conjugated.

The value of the methods indicated above are closely tied to the availability of suitable fluorescent compounds. In recent years, the evolution of solid state emitting diodes and solid state detectors has progressed rapidly as has the chemistry of fluorescent dyes. This evolution opened several opportunities for applications in the red and near infrared region (617 to 2500 nm). The red and near infrared region appears particularly suitable for biological analysis because of the low background fluorescence generated by biological material or by chemical compounds. Moreover, the development of inexpensive commercial diode lasers with emitting wavelengths of 670, 750, 780, and 810 nm, led to research into dyes that can be excited at these wavelengths.

Earlier efforts in this field produced many dyes, most of them belonging to the cyanine family. However, these dyes did not satisfy all the requirements needed for useful applications. Waggoner et al. (*Bioconjugate Chemistry*, 4, 105–111 (1993)) studied the chemistry of the cyanine dyes in order to develop conjugation sites and also to enhance water solubility. They synthesized sulfoindocyanine dyes with high hydrosolubility and reactive groups available for conjugation with biological compounds. However, these dyes cannot be excited by diode lasers and/or have low fluorescence quantum yields.

During the development of photo-sensitive dyes, a Kodak research group added one more ring to the indolenine moiety and made the dye structure more rigid by means of an additional ring in the polymethine chain. Trying to reach the same goal, Patonay et al. (*J. Org. Chem.*, 57, 4578–4580 (1992)) studied structures bearing activated groups for conjugation purposes and a chlorocyclohexenyl ring in the polymethine chain. The latter increases the rigidity of the structure, thus enhancing the fluorescence quantum yield of the dye. It also provides a convenient site for chemical substitution at the central ring, useful for introducing reactive groups or electron withdrawing radicals capable of modifying the excitation wavelength. Some of the drawbacks of Kodak's and Patonay's dyes are their low hydrophilicity and/or the mismatch with commercially available diode lasers.

The prior art is silent regarding the sulfo benz[e]indocyanine fluorescent dyes of the present invention as well as their uses in immunoassays, DNA probes, DNA sequencing, HPLC, capillary electrophoresis, fluorescence polarization, total internal reflection fluorescence, flow cytometry, and optical sensors. The above analytical techniques would enjoy substantial benefits when using the fluorescent dyes of the present invention, which have high quantum efficiency, absorption, and emission characteristics at the red and near infrared region, simple means for conjugation, and are substantially free of non-specific interference.

OBJECTS OF THE INVENTION

A primary object of the present invention is to provide sulfo benz[e]indocyanine fluorescent dyes.

An additional object of the present invention is to provide sulfo benz[e]indocyanine fluorescent dyes of high hydrophilicity having one or more sulfonic acid groups attached to the benzo ring.

A further objective of the instant invention is to provide sulfo benz[e]indocyanine fluorescent dyes having high quantum efficiencies.

Still another object of the present invention is to provide sulfo benz[e]indocyanine fluorescent dyes having reactive sites for conjugation.

Another object of the present invention is to provide sulfo benz[e]indocyanine fluorescent dyes having a rigidity enhancing central ring in the molecule.

A still further object of the instant invention is to provide sulfo benz[e]indocyanine fluorescent dyes having variable polymethine chains for tuning the fluorescent behavior of the dyes.

Another primary objective of the present invention is to provide biologically active molecules having attached thereon sulfo benz[e]indocyanine fluorescent dyes.

A further object of the present invention is to provide sulfo benz[e]indocyanine fluorescent dyes useful in the red and near infrared region.

An additional object of the instant invention is the use of the sulfo benz[e]indocyanine fluorescent dyes in biological assays.

SUMMARY OF THE INVENTION

The present invention is directed to fluorescent dyes and their valence tautomers of the formula:

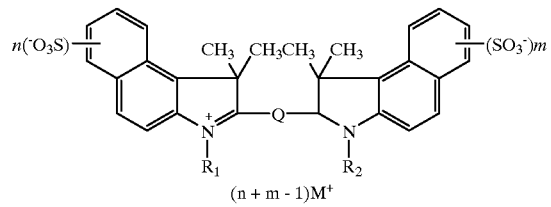

wherein Q represents a conjugated moiety that increases the fluorescent quantum yield of the compound; $R_1$ is a functionalized group of the formula $-(CH_2)_j Y$, wherein Y is selected from the group consisting of $SO_3H$, COOH, $NH_2$, CHO, NCS, epoxy, phthalimido, and COOZ, wherein Z represents a leaving group; $R_2$ is a functionalized group of the formula $-(CH_2)_k Y'$, wherein Y' is selected from the group consisting of $SO_3H$, COOH, $NH_2$, CHO, NCS, epoxy, phthalimido, and COOZ, wherein Z represents a leaving group; $M^+$ is a counterion selected from the group consisting of ammonium, alkali metal cations, and alkaline earth metal cations; n=1 to 4; m=1 to 4; j=2 to 10; and k=2 to 10.

The conjugated moiety Q is typically selected from the group consisting of:

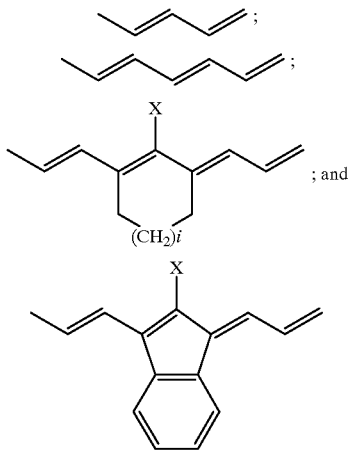

wherein X is selected from the group consisting of hydrogen, F, Cl, Br, I, and substituted aryl, wherein said aryl substituent is selected from the group consisting of $SO_3H$, COOH, $NH_2$, CHO, NCS, epoxy and COOZ, and wherein Z represents a leaving group; and i=0 or 1.

The instant invention is also directed to the use of the above fluorescent dyes to label biological molecules which are useful in biological assays.

Additional features and advantages of the invention are set forth in the description which follows and in part will be apparent from the description. The objectives and other advantages of the invention will be realized and attained by the fluorescent dyes of the invention and their uses as particularly pointed out in the written description, claims, and appended drawings.

It is to be understood that both the foregoing general description and the following detailed description are exemplary and explanatory and are intended to provide further explanation of the invention as claimed.

DETAILED DESCRIPTION OF THE INVENTION

Figure 1:
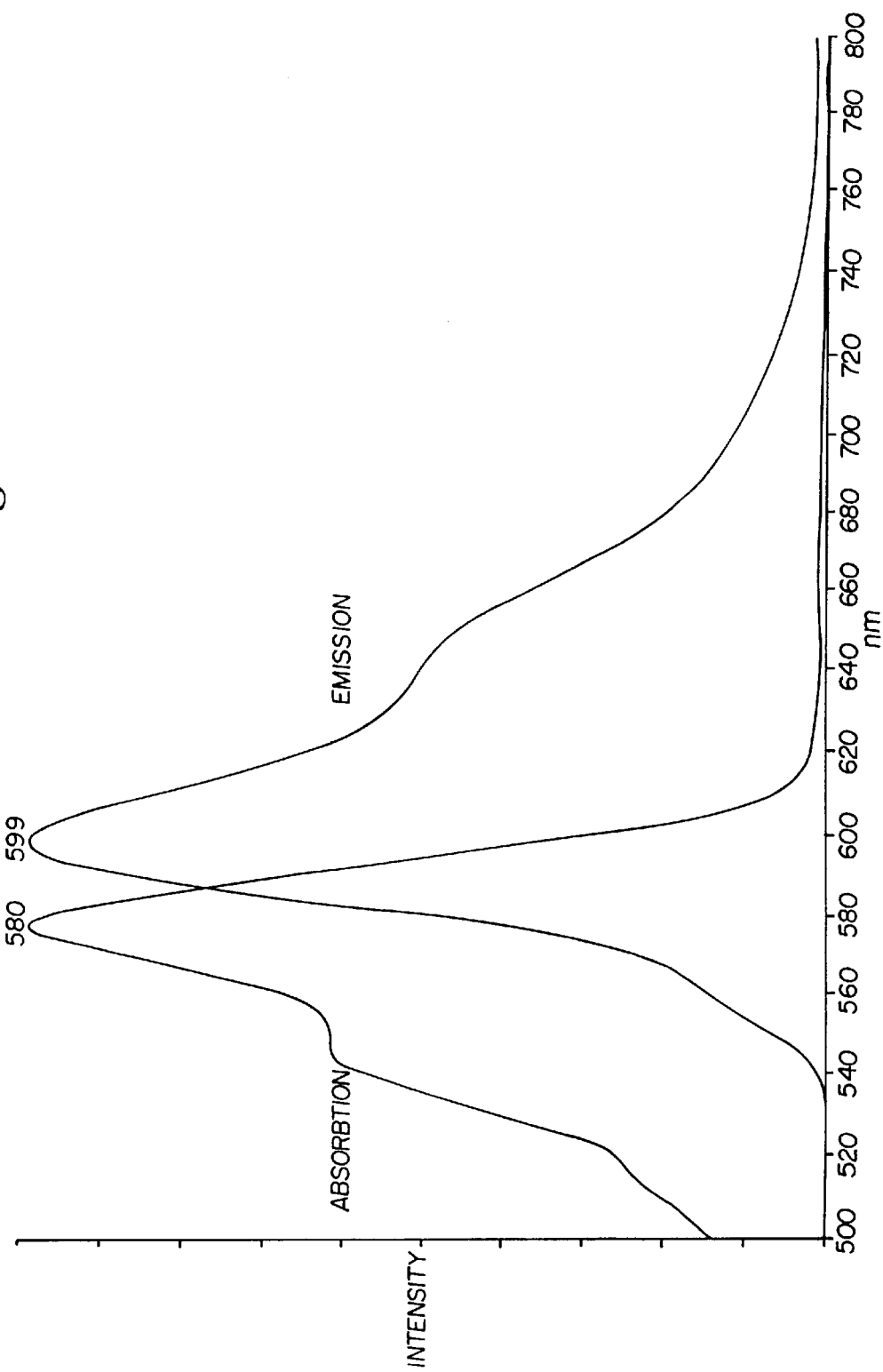
FIG. 1 shows the absorption and emission spectra of dye (7).
Figure 2:
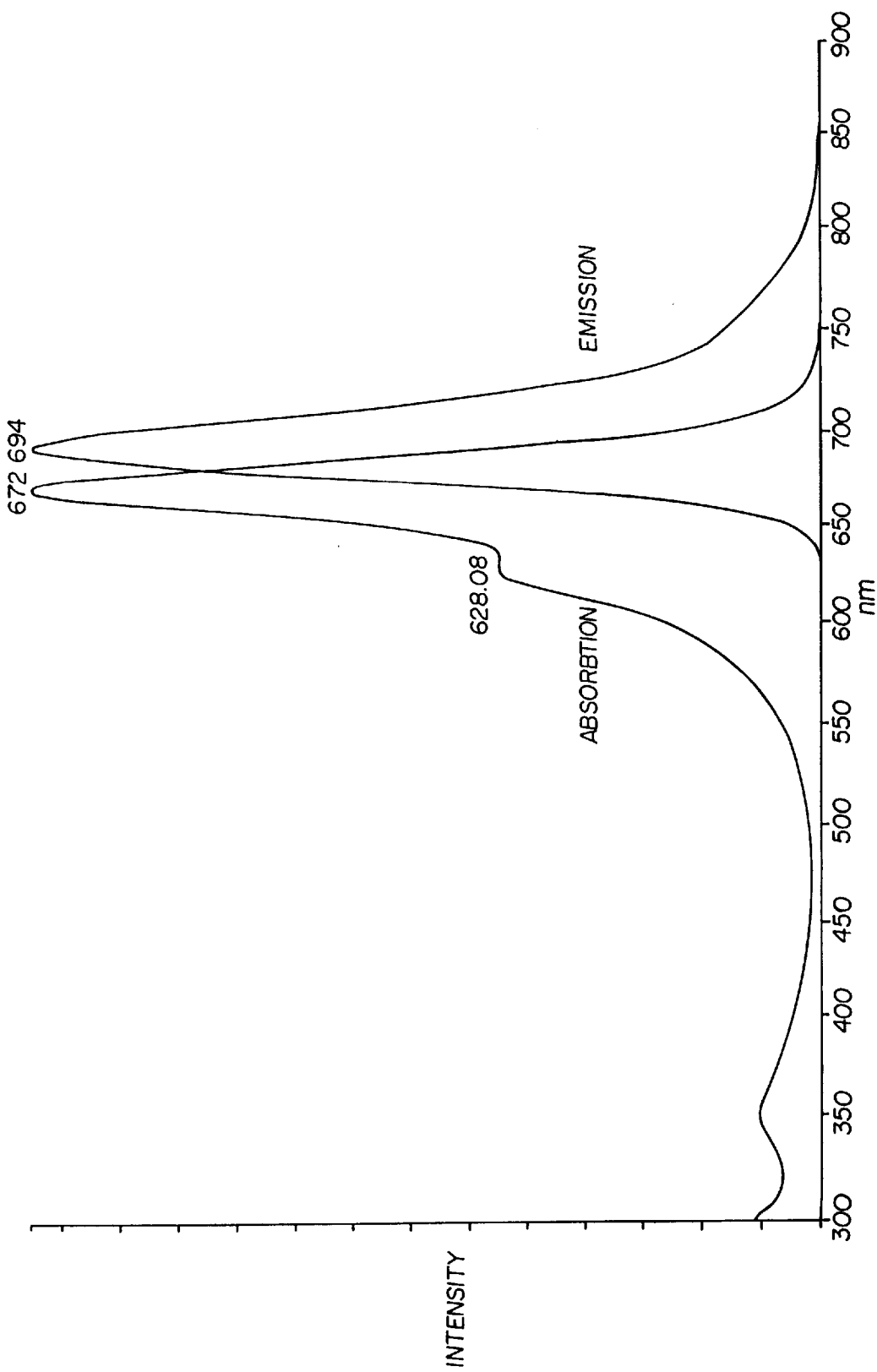
FIG. 2 shows the absorption and emission spectra of dye (8).
Figure 3:
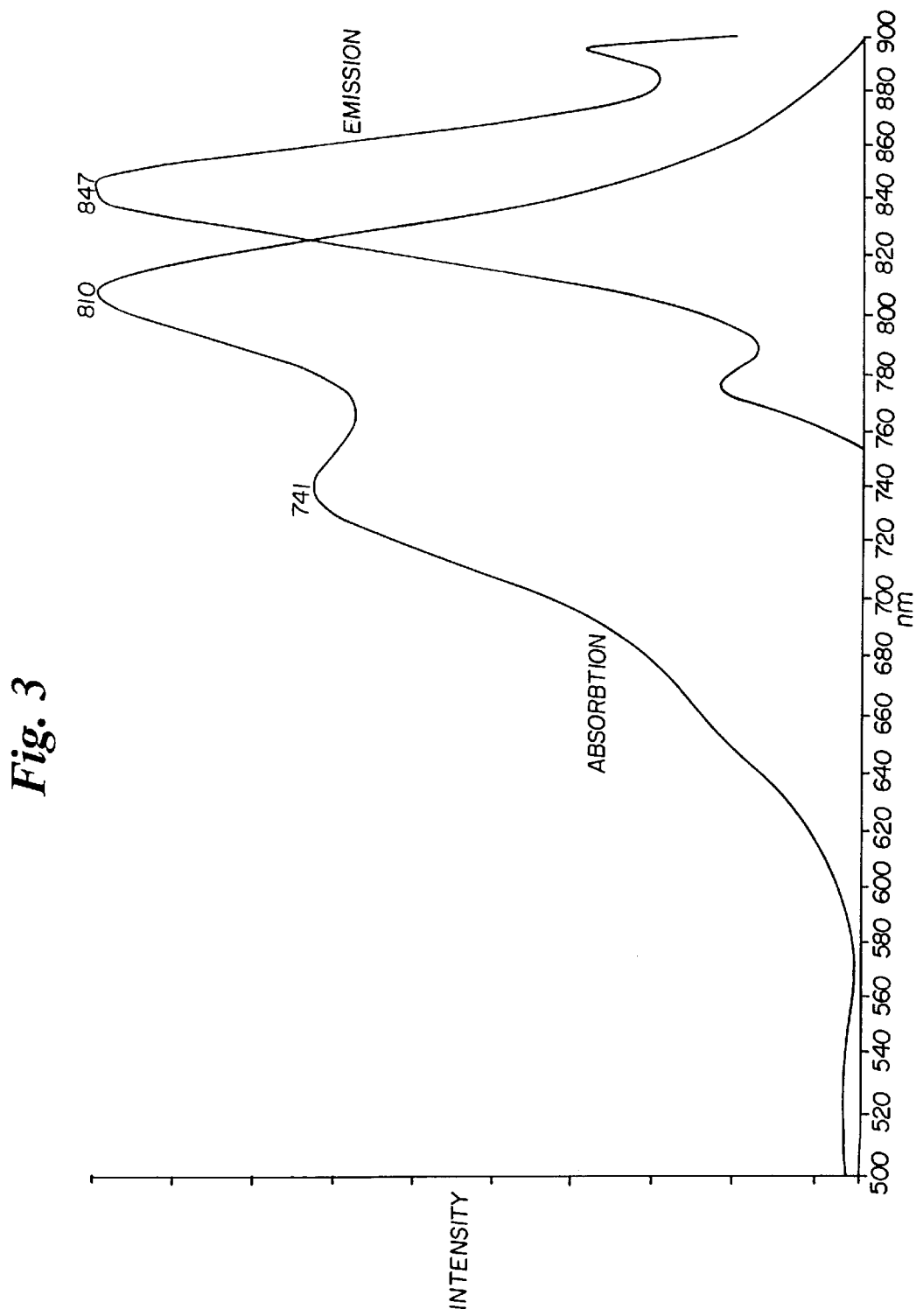
FIG. 3 shows the absorption and emission spectra of dyes (9) or (10).
Figure 4:
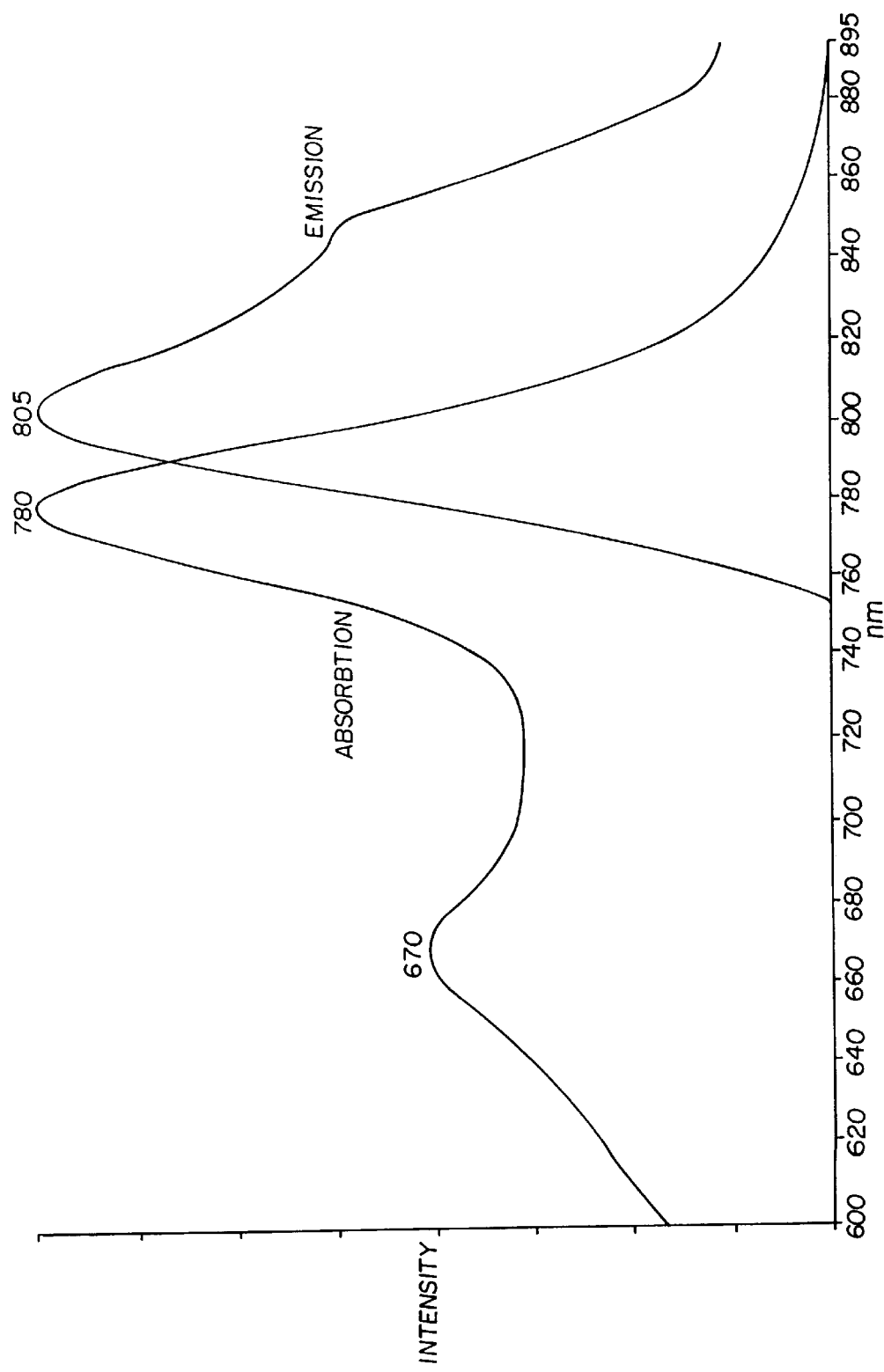
FIG. 4 shows the absorption and emission spectra of dye (10).

The present invention is directed to a fluorescent dye and its valence tautomers of the formula:

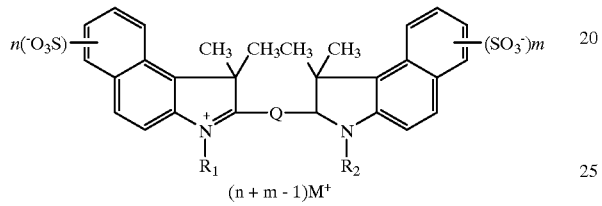

wherein Q represents a conjugated moiety that increases the fluorescent quantum yield of the compound; $R_1$ is a functionalized group of the formula —$(CH_2)_j Y$, wherein Y is selected from the group consisting of $SO_3H$, COOH, $NH_2$, CHO, NCS, epoxy, phthalimido, and COOZ, wherein Z represents a leaving group; $R_2$ is a functionalized group of the formula —$(CH_2)_k Y'$, wherein Y' is selected from the group consisting of $SO_3H$, COOH, $NH_2$, CHO, NCS, epoxy, phthalimido, and COOZ, wherein Z represents a leaving group; $M^+$ is a counterion selected from the group consisting of ammonium, alkali metal cations, and alkaline earth metal cations; n=1 to 4; m=1 to 4; j=2 to 10; and k=2 to 10. The conjugate moiety Q preferably also enhances the tuning behavior of the compound.

The conjugate moiety Q is preferably selected from the group consisting of:

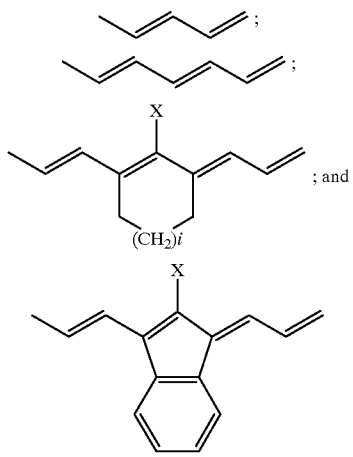

wherein X is selected from the group consisting of hydrogen, F, Cl, Br, I, and substituted aryl, wherein said aryl substituent is selected from the group consisting of $SO_3H$, COOH, $NH_2$, CHO, NCS, epoxy and COOZ, and wherein Z represents a leaving group; and i=0 or 1.

More specifically, the fluorescent labeling dyes of the present invention can be represented by the following general formulae:

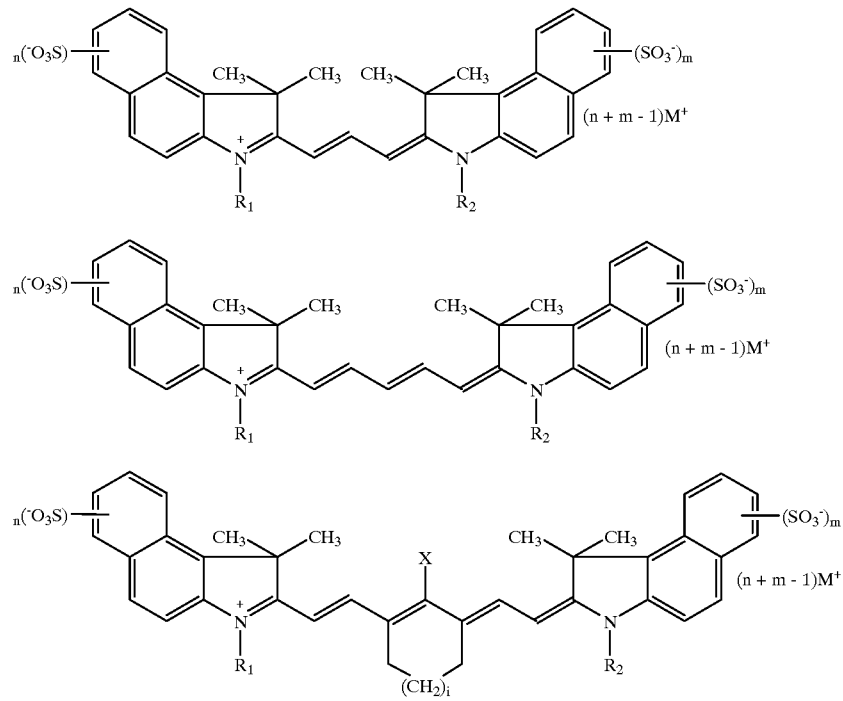

-continued

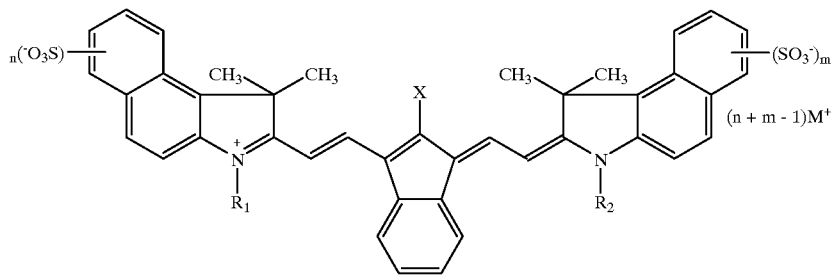

wherein $R_1$ is a functionalized group of the formula —$(CH_2)_j Y$, wherein Y is selected from the group consisting of $SO_3H$, COOH, $NH_2$, CHO, NCS, epoxy, phthalimido, and COOZ, wherein Z represents a leaving group; $R_2$ is a functionalized group of the formula —$(CH_2)_k Y'$, wherein Y' is selected from the group consisting of $SO_3H$, COOH, $NH_2$, CHO, NCS, epoxy, phthalimido, and COOZ, wherein Z represents a leaving group; M is a counterion selected from the group consisting of ammonium, alkali metal cations and alkaline earth metal cations; n=1 to 4; m=1 to 4; j=2 to 10; k=2 to 10; i=0 or 1 and wherein X is selected from the group consisting of hydrogen, F, Cl, Br, I, and substituted aryl, wherein said aryl substituent is selected from the group consisting of $SO_3H$, COOH, $NH_2$, CHO, NCS, epoxy, and COOZ, wherein Z represents a leaving group.

The leaving group Z is basically any organic leaving group which can be easily displaced when the fluorescent dyes of the present invention are attached or conjugated to a specific molecule, e.g., an antibody. A typical leaving group is n-hydroxysuccimide. The fluorescent dyes of the present invention can be symmetrical, i.e., $R_1$ and $R_2$ are identical, or asymmetrical, i.e., $R_1$ and $R_2$ are not identical.

Valence tautomerism means the shifting of the conjugated bonds as shown below for an asymmetric fluorescent dye:

1. One or more sulfonic groups attached to the benzo ring to give high hydrophilicity to the compound and suppress non-specific binding to proteins and surfaces, including skin, thus allowing its use as a biochemical label. In addition, the negative charge borne by the sulfonic groups helps reduce the stacking between dye molecules by means of electrostatic repulsion. Such stacking is known to reduce the fluorescence quantum yield of the dye.
2. The presence of the ring increases the rigidity of the structure and therefore increases the quantum yield of fluorescence.
3. The groups bonded at the N in 1 or 1' position (generally carboxyalkyl, sulfoalkyl or alkylamine chains) have reactive sites for conjugation purposes or in order to increase solubility in aqueous media.
4. The central ring increases the rigidity of the dye, thus enhancing its fluorescence quantum yield. The central ring also hinders attack by oxygen, therefore increasing the stability of the dye with respect to oxidation. It can be used to introduce substituents with reactive sites for conjugation purposes or in order to increase solubility in aqueous media.
5. The polymethine chain length present in the dye provides the main tool for tuning the fluorescent behavior of this class of dyes.

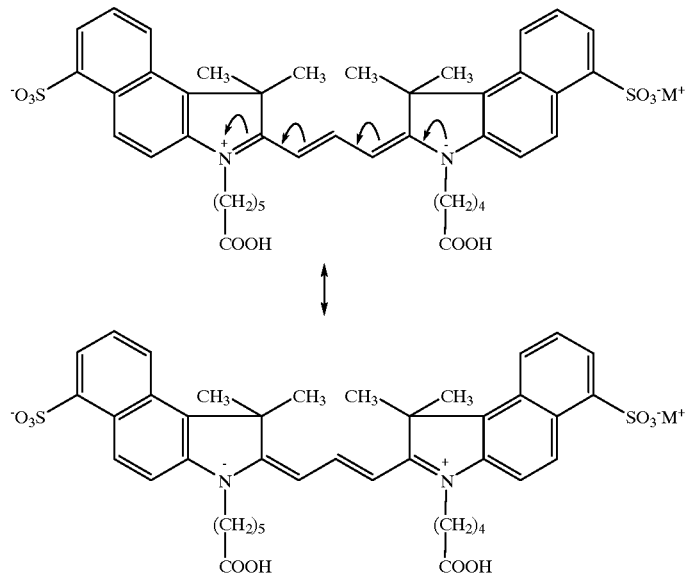

The fluorescent dyes of the instant invention have the following important features:

The compounds of the present invention are synthesized by starting with the new compound 2,3,3-trimethyl benz[e]indolenine-7-sulfonic acid (4). The synthesis of compound (4) is outlined in Scheme I below:

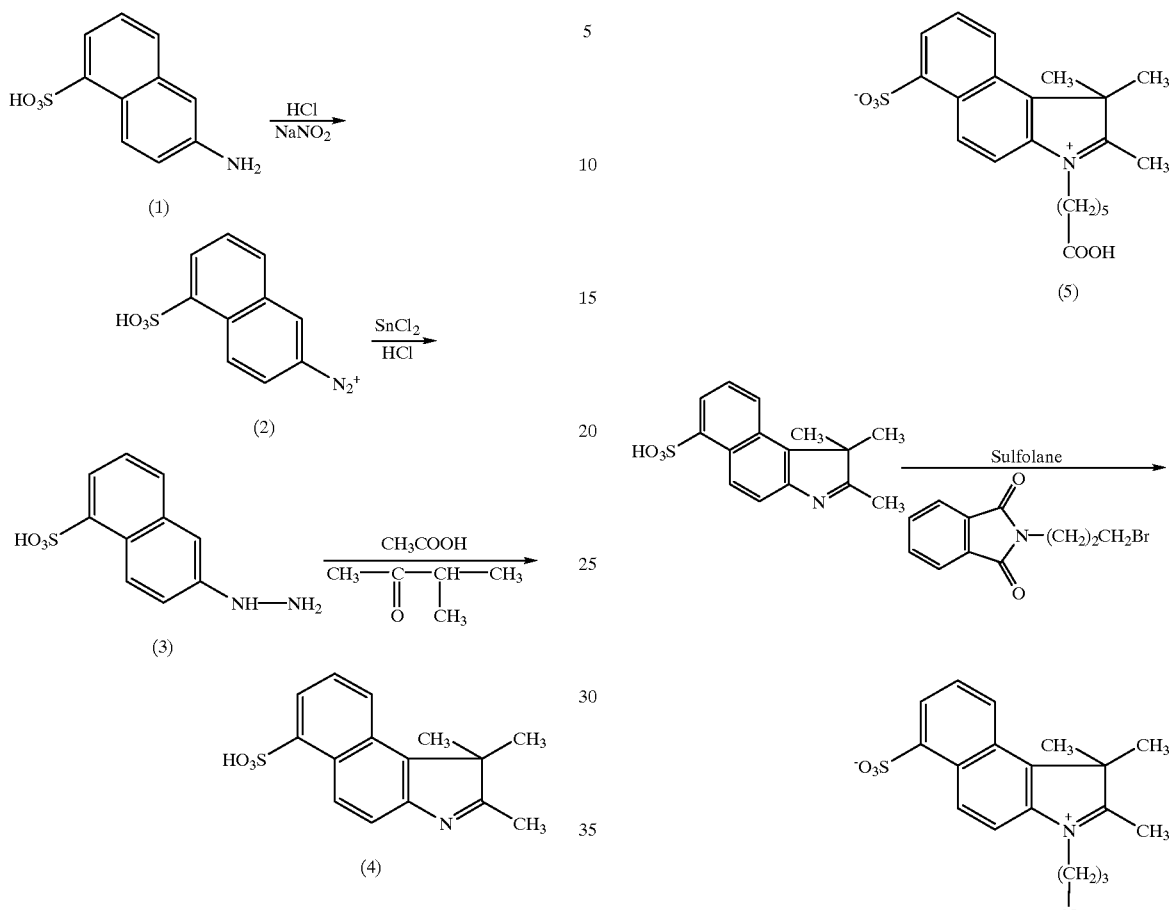

Starting with compound (4) a multiple number of intermediates such as compounds (5) and (6) can be synthesized as shown in Scheme II below:

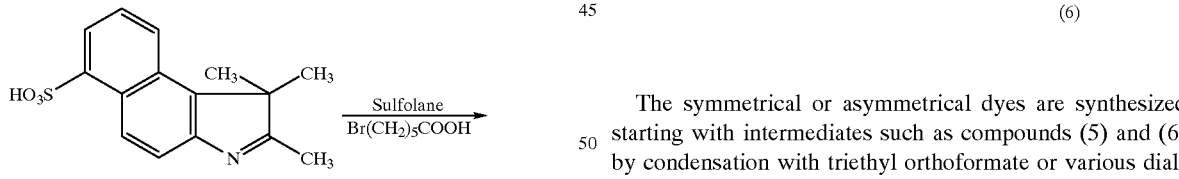

The symmetrical or asymmetrical dyes are synthesized starting with intermediates such as compounds (5) and (6) by condensation with triethyl orthoformate or various dialdehyde dianilides as shown in Scheme III below:

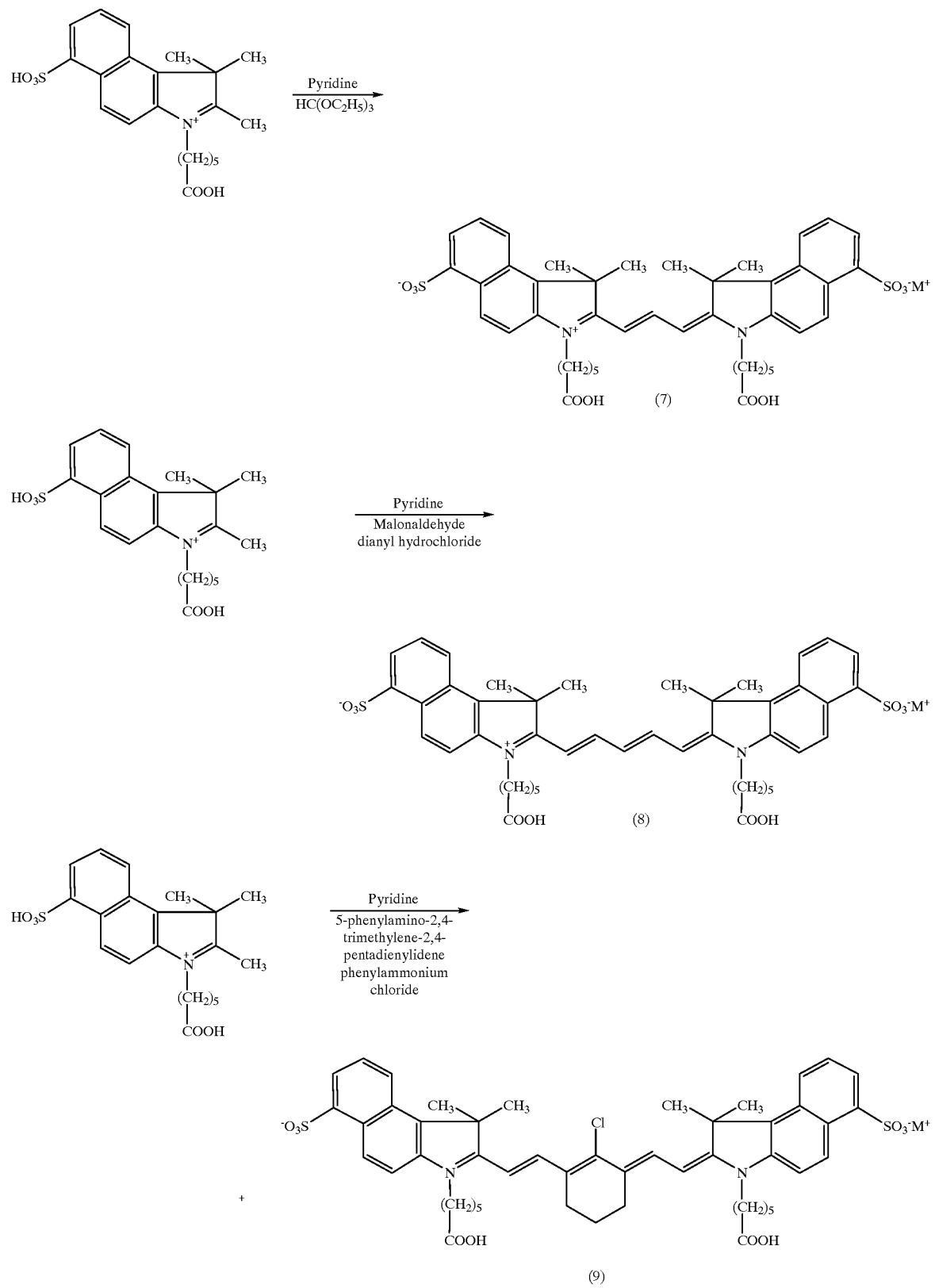
Scheme III

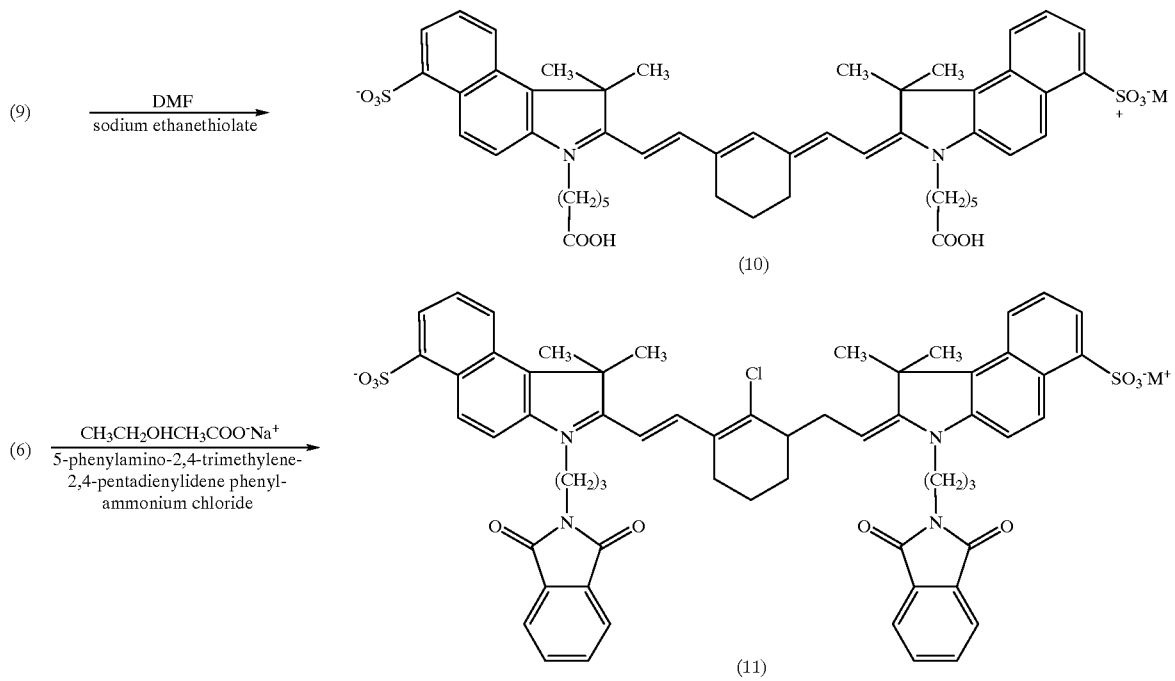

As noted above, the cyanine dyes were synthesized starting from a new intermediate, the 2,3,3-trimethyl benz[e] indolenine-7-sulfonic acid. From this molecule different cyclammonium quaternary salts were obtained, and the latter were condensed with compounds such as triethyl orthoformate or various dialdehyde dianilides. The side chains attached to the 1- and 1'-nitrogen atoms of the benz[e]indolenine may be the same or different, leading to symmetrical or asymmetrical dyes. All these compounds are usually in the salt form and the counter-ion ($M^+$) depends on reaction and purification conditions. It should be noted that as with other cyanine dyes, the dyes of the present invention may exist as monomers, H-aggregates and J-aggregates, depending on the chemical equilibrium involved. Of course the pKa and pH will have a substantial effect as to the form which the dye takes when dissolved in a given solvent. Additionally, an equilibrium also exists between monomers and aggregates consisting of dimers, trimers, or higher polymers. Factors such as ionic strength, dye concentration, temperature and solvent effect the equilibrium.

The fluorescent dyes of the present invention combine all the optimum properties that are desirable in these types of dyes. The desirable properties of these dyes include absorption maxima matching light emitting diodes and laser diodes (see Table I and FIGS. 1 to 4), emission maxima in the low background red and near infrared spectral region; and chemical properties fulfilling labeling requirements (such as presence of reactive sites, hydrosolubility, lack of non-specific binding to proteins and surfaces, including skin, and stability).

TABLE I

| DYE | ABSORPTION ($\lambda_{MAX}$) | EMISSION ($\lambda_{MAX}$) | COMMERCIAL LIGHT EMITTING DIODES/LASER DIODES:EMITTING WAVELENGTH |
| --- | --- | --- | --- |
| (7) | 580 | 599 | 585 |
| (8) | 672 | 694 | 670 |
| (9) or (11) | 741, 810 | 847 | 750, 810 |
| (10) | 670, 780 | 805 | 670, 780 |

As mentioned in the background of the present invention, the fluorescent dyes of the present invention are particularly useful in clinical chemistry, immunochemistry and analytical chemistry. The compounds can be used in fluorometric immunoassays, DNA probes, high pressure liquid chromatography (HPLC), capillary electrophoresis, fluorescence polarization, total internal reflection fluorescence (T.I.R.F.), flow cytometry, DNA sequencing, and optical sensors. When the fluorescent compounds of the present invention are used in immunochemical determinations, it is typically necessary to conjugate the fluorescent label to one of the binding partners, e.g., an antibody or an antigen or a biologically active protein molecule.

Depending upon the molecule being labeled, a wide variety of linking groups may be employed for conjugating the protein to the other molecule. For the most part, with small molecules the functional group of interest for linking will be carbonyl, either an aldehyde to provide for reductive amination or a carboxyl, which in conjunction with carbodiimide or as an activated ester, e.g., N-hydroxy succinimide, will form a covalent bond with the amino groups present in the protein. Another useful functional group is a thio ether or disulfide, where the protein may be modified with an activated olefin and a mercapto group added or activated mercapto groups joined, e.g., Ellman's reagent, isothiocyanate, diazonium, nitrene, or carbene. There is ample literature for conjugating a wide variety of compounds to proteins. See, for example, A. N. Glazer, *The Proteins, Vol. IIA,* 3rd Ed., N. Neurath and R. L. Hill, eds., Academic Press, pp. 1–103 (1976); A. N. Glazer et al., "Chemical Modification of Proteins," *Laboratory Techniques in Biochemistry and Molecular Biology,* Vol. 4, PRT 1, T. S. Work and E. Work, eds., North-Holland Publishing Co. (1975); and K. Peters et al., *Ann. Rev. Biochem.,* 46, 423–51 (1977), the descriptions of which are incorporated by reference herein. Examples of commercially available cross-linking reagents are disclosed in the Pierce 1981–82 Handbook and General Catalog, pp. 161–166, Pierce Chemical Co., Rockford, Ill.

As indicated above, antigens or antibodies are labeled with the fluorescent dyes of the invention by ordinary chemical reaction. Thus, a fluorescent dye can be reacted with an antigen or antibody to form a labeled reaction product by covalent linkage; specifically, the reaction occurs between the functional group (i.e., mercapto, amino, hydroxy, or carboxy) of the dye and an amino, imino, mercapto, carboxy, carboxylic acid amide, or hydroxy group (s) of an antigen or antibody. The reaction between the two can be carried out by any of the following procedures:

(1) Fluorescent dyes are directly reacted with the functional groups;

(2) Fluorescent dyes and the functional groups are reacted using an activating agent; or (3) Fluorescent dyes and the functional groups are reacted through at least one compound having a bifunctional group.

Groups which are reactive with the functional groups of antigens or antibodies and methods for reacting the same are described in detail, in, e.g., *Lectures on Experimental Biochemistry,* vol. 1 subtitled "Chemistry of Proteins", vol. 2, subtitled "Chemistry of Nucleic Acids", vol. 3, subtitled "Chemistry of Lipids" and vol. 4, subtitled "Chemistry of Sugars", all edited by the Biochemical Association, Japan, published by Tokyo Kagaku Dojin (1977); Izumiya, *Peptide Gosei* (Peptide Synthesis); and Greenstein et al., *Chemistry of the Amino Acids,* vols. I–III (1961), John Wiley & Sons Inc., New York. One skilled in the art can easily perform such reactions for forming the linking from knowledge in the art and these publications.

Examples of compounds containing groups which react with the functional groups described above further include, e.g., activated esters, activated halogens, aldehydes, activated vinyl esters, activated halogens, aldehydes, activated vinyl compounds, acid anhydrides, acid halides, thioisocyanates, isocyanates, carboxylic acids, amides, alkyl halides, nitrophenyl halides, etc. Accordingly, these functional groups can originally be present in the fluorescent dyes or can be introduced as a result of the reaction of a compound having a bifunctional group and the fluorescent dye.

Reaction conditions for labeling vary depending upon the kind of the antigen or antibody, the kind of fluorescent dye etc., and conditions are selected so as to not damage the biological activity of the antigen or antibody to be labeled. Accordingly, the reaction temperature is generally chosen from the range of from 40 to 60 C, preferably −20 to 40 C; and the reaction time from the range of from 10 minutes to 16 hours. The reaction pressure is preferably atmospheric pressure, but can suitably be chosen from the range of 1 to 20 atmospheres. It is advantageous that water or a pH buffer solution be used as a solvent for the labeling. Organic solvents such as DMF (dimethylformamide), methylene chloride, etc., can also be employed. These reaction conditions are common to reaction conditions which are generally applicable to modification of proteins or enzymes and details are described in the publications referred to above.

The amount of fluorescent dyes used for labeling varies depending upon the kind of substances to be labeled, but is generally in a molar ratio of $1/100$ to 100 moles per 1 mole of the antigen or antibody, preferably $1/20$ to 20 times per 1 mole of the antigen or antibody, more preferably ½ to 2 times per 1 mole of the antigen or antibody.

Useful methods for confirming completion of labeling include methods for measuring spectra such as UV, visible rays, IR, mass, and NMR spectra, etc., and a method confirming labeling via disappearance of the terminal group at which the labeling substance is to be introduced. Simple tests will be enough to confirm completion of labeling. Where it is confirmed utilizing absorption spectrum, following completion of the labeling reaction, an absorption spectrum of a separated and purified product is measured; if the resulting absorption spectrum is consistent with the intrinsic absorption spectrum which a fluorescent dye possesses, it is confirmed that the labeling reaction was effected. A further method for confirming the labeling being effected is to analyze for the presence or absence of the specific terminal groups, e.g., an amino or carboxy group(s).

The terminal carboxy group(s) are analyzed to check completion of the labeling reaction, details of which are given in e.g., S. Akabori, K. Ohno and K. Narita, *Bull. Chem. Soc. Japan,* 25, 214 (1952) (generally referred to as a hydrazine decomposition method in the art); H. Matuo, U. Fujimoto and T. Tatuno, *Biochem. Biophys. Res. Communication,* 22, 69 (1966) (a tritium marking method); etc. Further, details of these terminal determination methods are also given as a review in S. B. Needleman, *Protein Sequence Determination,* published by Springer Verlag (Berlin), 1975.

The protein molecules such as the antibodies or antigens can be used in an immunochemical determination according to one of the preferred aspects of the invention. A typical fluorometric immunoassay of an antigen in a liquid sample comprises incubating a mixture of:

(a) the liquid sample;

(b) labelled antibodies to the antigen under assay;

(c) a reagent comprising antibodies to the antigen under assay; and (d) a reagent capable of binding to component(c) by non-covalent bonding, but which is not directly bindable to either component (a) or component (b). The reagent (d) is bound to a solid phase support. At least one of components (b), (c) and (d) comprises monoclonal antibodies. The solids fraction is separated from the liquid fraction and the amount of label in one of the fractions is determined. From the amount of the label, the amount of antigen present in the sample is determined. The antibody reagents may also be used in the form of fragments.

Another aspect of the invention is a competitive assay for determining the amount of an antigen in a sample suspected of containing the antigen comprising: (a) incubating the sample with a solution of a fluorescent-labeled antigen, anti-antigen antibody, and an antibody against the anti-antigen antibody; (b) adding a nonfluorescent nonlight-scattering immunoprecipitant to the incubation mixture to form an immunoprecipitate; (c) separating the immunoprecipitate and dissolving the immunoprecipitate in a nonfluorescent solvent that has a low ionic strength and maintains the pH of the resulting solution substantially constant; and (d) measuring the fluorescence intensity of the solution of step (c) and comparing the fluorescence intensity to a standard curve.

Typically the sample that is analyzed is a body fluid such as blood, blood serum, blood plasma, urine, lymph fluid, bile, spinal fluid, or the like. The particular body fluid analyzed may vary with the antigen being assayed. In most instances blood serum will be used. About 0.1 to about 500 $\mu$l of fluid is typically used per assay.

Substances that may be assayed by the use of the fluorescent labeling reagents of the present invention include antigens (molecules that elicit an immune response when introduced into the bloodstream of a vertebrate host) and haptens that are not immunogenic per se but may be conjugated to a protein carrier to form a conjugate that is immunogenic and capable of raising antibodies against the hapten. The term "antigen" is used herein to generically denote both antigenic and haptenic compositions. Such substances include drugs, hormones, pesticides, toxins, vitamins, human bacterial and viral proteins, and the like. Examples of antigens that may be assayed by the invention include thyroxine ($T_4$), triodothyronine ($T_3$), digoxin, gentamycin, amikacin, tobramycin, kanamycin, cortisol, luteinizing hormone, human chorionic gonadotropin, theophylline, angiotensin, human growth hormone, HIV infection, $\alpha$ fetoprotein, and the like.

The reagents that are incubated with the sample suspected of containing antigen to form immune complexes typically are (1) fluorescent-labeled antigen, (2) anti-antigen antibody, (3) antibody against the anti-antigen antibody, and (4) a nonfluorescent non-light-scattering immunoprecipitant (e.g., polyethylene glycol). A stated above, the fluorescent-labeled antigen may be made by coupling the antigen with a reactive derivative of the fluorescent dye using multifunctional coupling agents such as aldehydes, carbodiimides, dimaleimides, imidates, and succinimides.

The dyes of the present invention also have utility in any current application for detection of nucleic acids that requires a sensitive detection reagent. In particular, the dyes are useful for the detection of cell-free isolated nucleic acids, nucleic acids in solution, and nucleic acid bands in gels. Additionally, the present dyes greatly increase the sensitivity of detection of nucleic acids in a variety of cells and tissues, both living and dead, plant and animal, eukaryotic and prokaryotic. This family of dyes displays unusually good photostability and appears to be relatively non-toxic to cells. Furthermore, many of the dyes rapidly penetrate cell membranes of a variety of cells. The dyes of the invention exhibit superior properties compared to the known cyanine dyes.

The use of the fluorescent dyes of the present invention in the detection of nucleic acids typically comprises combining a dye of the present invention with a sample that contains a nucleic acid, incubating the sample for a time sufficient to obtain a detectable fluorescent response, and observing the fluorescent response.

Typically, the dye is present as a staining solution, which is prepared by addition of the dye to an aqueous solution that is biologically compatible with the sample. The staining solution is made by dissolving the dye directly in an aqueous solvent such as water; a buffer solution such as phosphate buffered saline; an organic water-miscible solvent such as dimethylsulfoxide (DMSO), dimethylformamide (DMF), or acetonitrile; or a lower alcohol such as methanol or ethanol. Typically the dye is preliminarily dissolved in an organic solvent (preferably DMSO) at a concentration of greater than about 100 times that used in the staining solution, then diluted one or more times with an aqueous solvent such as water or buffer. Preferably, the dye is dissolved in about 100% DMSO and then diluted one or more times in water or buffer such that the dye is present in an effective amount. An effective amount of dye is an amount sufficient to give a detectable fluorescent response when in the presence of nucleic acids. Typically staining solutions for cellular samples have a dye concentration greater than about 0.1 nM and less than about 100 $\mu$M, more typically greater than about 1 nM. Staining solutions for electrophoretic gels typically have a dye concentration of greater than about 1 $\mu$M and less than about 10 $\mu$M, more typically about 4 to 5 $\mu$M. It is generally understood in the art that the specific concentration of the staining solution is determined by the physical nature of the sample, and the nature of the analysis being performed.

The dye is combined with a sample that contains a nucleic acid. The nucleic acid in the sample may be either RNA or DNA, or a mixture thereof. When the nucleic acid present is DNA, the DNA may optionally be single-, double-, triple-, or quadruple-stranded DNA. The nucleic acid may be either natural (biological in origin) or synthetic (prepared artificially). The nucleic acid may be present as nucleic acid fragments, oligonucleotides, or nucleic acid polymers. The nucleic acid may be present in a condensed phase, such as a chromosome. The presence of the nucleic acid in the sample may be due to a successful or unsuccessful experimental methodology, undesirable contamination, or a disease state. Nucleic acid may be present in all, or only part, of a sample, and the presence of nucleic acids may be used to distinguish between individual samples, or to differentiate a portion or region within a single sample.

The fluorescent dyes of the present invention can also be used for DNA sequencing methods. The method is based on Sanger's chain terminating sequencing method as described in Sanger et al., *Proc. Natl. Acad. Sci.* 74, 5464 (1977), the contents of which are incorporated by reference herein. Typically, a fluorophore-labeled probe specific to the sequence is hybridized with the target DNA and the sequence ladders are identified by laser induced fluorescence or other appropriate means for detecting fluorescent labeled DNA.

The fluorescent dyes of the invention are also useful in assay methodologies that employ DNA probes for the determination of the presence and/or quantity of analytes. More particularly, an assay method for an analyte in a sample utilizing a DNA probe labeled with a dye of the invention comprises contacting the DNA probe thus labeled under suitable conditions for binding with the analyte, where the binding is representative of the presence or amount of the analyte in the sample, and determining the extent of the binding by measuring the fluorescence of the fluorescently labeled DNA probe. As an embodiment of this method, the analyte to be determined can be separated from the sample in which it is present prior to being bound by the DNA probe. It is also possible to employ first and second DNA probes in a single assay, where the first of such probes is bound with a fluorescent dye according to the invention, and the second probe is not labeled and is bound to a solid phase. In this way the analyte can be separated from the sample by contacting the sample with the second DNA probe under conditions suitable for binding the analyte therewith, and the remaining sample is removed prior to contacting the analyte with the first (labeled) DNA probe.

It is also within the scope of the assay methods utilizing the fluorescent dyes of the present invention that the step of separating the analyte from the sample in the manner just described can also be practiced with labeled binding reagents other than DNA probes. For example, instead of utilizing first (labeled) and second (unlabeled and bound to a solid phase) DNA probes, plural immunologically binding reagents specific for a given analyte can be used.

Additionally, the fluorescent dyes of the present invention can be used in flow cytometry. The method is characterized by the use of a flow cytometer that comprises a light source, a flow cell that permits the blood cells in a sample to flow one by one through a constricted channel, a photometric unit that detects light issuing from each blood cell, and an analyzer for analyzing the detected signal. In this method, the corpuscles in the sample which are stained are illuminated under light and the fluorescence emitted from the irradiated corpuscles is detected, optionally together with scattered light, with leukocyte classification being made in accordance with the intensity of the detected signal. The examples below are given to illustrate the practice of this invention. They are not intended to limit or define the entire scope of this invention.

EXAMPLES

For the synthesis of the common intermediate, 2,3,3-trimethyl benz[e]indolenine-7-sulfonic acid, we started with Dahl's acid, 6-amino-1-naphthalensulfonic acid, and through diazotization and reduction we converted it to 6-hydrazino-1-naphthalensulfonic acid; then, by classical Fischer indole synthesis with 3-1-ethyl-2-butanone we obtained 2,3,3-trimethyl benz[e]indolenine-7-sulfonic acid. It is remarkable that the cyclization takes place yielding just the desired isomer.

Example 1

Diazotization of Dahil's Acid.

A suspension of 13.34 g (64.2 mmol) of Dahl's acid in 45 ml of concentrated hydrochloric acid was cooled to −5 C by an ice-salt bath in a 500 ml three-necked flask equipped with mechanical stirrer, thermometer and reflux condenser. To the slurry was added dropwise, at 0 C or below, an ice-cold sodium nitrite solution (4.43 g, or 64.2 mmol, in 30 ml of water) and the mixture was stirred for 40 minutes at the same temperature and then used without delay in the following step.

Example 2

Reduction of Diazotized Dahl's acid to 6-hydrazino-1-naptalenesulfonic acid (3).

A solution of stannous chloride dihydrate (43.6 g or 193.2 mmol) in 46 ml of cold concentrated hydrochloric acid was added dropwise at about 0 C, with stirring, to the slurry obtained by adding 50 g of chopped ice to the diazotized Dalil's acid. The addition requires almost 1 hour. The mixture was stirred for another 15 minutes. The slurry was refrigerated overnight, filtered, and washed with brine. The final product was recrystallized from hot water to yield 9.9 g (~64%). The $^1$H-NMR spectrum of the product was consistent with the structure of 6-hydrazino-1-naptalenesulfonic acid.

Example 3

Fischer synthesis of 2,3,3-trimethyl benz[e]indolenine-7-sulfonic acid (4).

To a 250 ml round-bottomed flask, equipped with reflux condenser and magnetic stirrer were added acetic acid (25 ml), 3-methyl-2-butanone (13.4 ml or 124 mmol) and 6-hydrazino-1-naphthalenesulfonic acid (9.9 g or 41.6 mmol). The mixture was dissolved and heated to reflux for 3 hours. Then the solution was evaporated and the residue washed with three n-hexane portions. The solid residue was dried, redissolved in methanol, and precipitated in ether to yield 2,3,3-trimethyl benz[e]indolenine-7-sulfonic acid (80%). As confirmed by the $^1$H-NMR spectrum, the cyclization occurred only at the 5-position of the naphthalene ring.

For the quaternarization we used methods described previously in the literature for similar compounds. All structures were confirmed by $^1$H-NMR.

Example 4

Synthesis of 1-(5'-carboxypentyl)-2,3,3-trimethyl benz[e]indoleninium-7-sulfonate (5).

In a 100 ml round-bottomed flask, 2.1 g (7.26 mmol) of 2,3,3-trimethyl benz[e]indolenine-7-sulfonate were dissolved in 27 ml of hot sulfolane under argon. To this solution was added 6-bromohexanoic acid (1.76 g or 9.0 mmol). The resulting mixture was then heated at 130 C for 12 hours. After cooling, the brown solution was mixed with toluene (~50 ml) and a dark solid separated; the solid was filtered and washed with two more portions of toluene. Excess toluene was distilled off as azeotropic mixture with ethanol. The product, dissolved in few milliliters of methanol, was precipitated by dropwise addition to a large excess of ether (yield ~35%).

Example 5

Synthesis of 1-[3'-(N-phthalimidopropyl)]-2,3,3-trimethyl benz[e]indoleninium-7-sulfonate (6).

In a round-bottomed flask were dissolved 2,3,3-trimethyl benz[e]indolenine-7-sulfonate (3 g or 10.4 mmol) and N-(3-bromopropyl)-phthalimide (2.78 g or 10.4 mmol) in sulfolane (~20 ml) and suspended 0.58 g (10.4 mmol) of KOH. The mixture was heated to 120 C for 6 hours. A solid was then precipitated from the solution by adding 50 ml of toluene. The solid was collected on a sintered glass filter and washed with toluene. The gummy residue was dissolved in ethanol and reprecipitated into ether to obtain a solid that was then thoroughly triturated with ethanol.

To obtain the free amine group it is possible to follow classical cleavage pathways such as treatment in ethanol with hydrazine at 25 C for 12 hours or hydrolysis in concentrated hydrochloric acid. Finally, the cyanine dyes can be obtained by condensing the benz[e]indoleninium-7-sulfonate intermediates with triethyl orthoformate or various dialdehyde dianilides.

Example 6

Synthesis of 2-{3'-[1"-(ε-carboxypentyl)-3",3"-dimethyl-7"-sulfobenz[e]indolin-2"-ylidene]-1-propen'-1'-yl}-1-(ε-carboxypentyl)-3,3-dimethyl benz[e]indoleninium-7-sulfonate (7).

In a round-bottomed flask equipped with a reflux condenser, 306 mg (0.76 mmol) of 1-(5'-carboxypentyl)-2,3,3-trimethyl benz[e]indoleninium-7-sulfonate were dissolved in 1 ml of pyridine. The solution was then heated to reflux. An excess of triethyl orthoformate (225 mg or 1.52 mmol) was added and the solution was refluxed for 2 hours. The mixture was cooled and the product was separated by addition of ether. The solid was dissolved in methanol and reprecipitated with ether (yield 56%).

Example 7

Synthesis of 2-{5'-[1"-(ε-carboxypentyl)-3",3"-dimethyl-7"-sulfobenz[e]indolin-2"-ylidene]-1',3"-pentadien-1'-yl}-1-(ε-carboxypentyl)-3,3-dimethyl benz[e]indoleninium-7-sulfonate (8).

Malonaldehyde dianil hydrochloride (160 mg or 0.620 mmol) was dissolved in a hot mixture of 5 ml acetic anhydride and 1.2 ml pyridine, in a 50 ml round-bottomed flask equipped with a reflux condenser. 1-(5'-carboxypentyl)-2,3,3-trimethyl Benz[e]indoleninium-7-sulfonate in an amount of 0.5 g (1.24 mmol) was added to the mixture. After 15 minutes, the solution was cooled and diluted with ether; a solid separated and was redissolved in a minimum volume of methanol and precipitated with a 2:1 2-propanol/ether mixture (yield 46%).

Example 8

Synthesis of 2-{5'-chloro-7'-[1"-($\epsilon$-carboxypentyl)-3",3"-dimethyl-7"-sulfobenz[e]indolin-2"-ylidene]-3',5'-(propane-1'"3'"-diyl}-1',3',5'-heptatrien-1'-yl}-1-($\epsilon$-carboxypentyl)-3,3-dimethyl benz[e]indoleninium-7-sulfonate (9).

A solution of (5-phenylamino-2,4-trimethylene-2,4-pentadienylydene) phenylammonium chloride (0.29 g or 0.80 mmol), 1-(5'-carboxypentyl)-2,3,3-trimethyl benz[e] indoleninium-7-sulfonate (0.65 g or 1.61 mmol) and sodium acetate (0.16 g or 1.93 mmol) in ethanol (30 ml) was heated to reflux for 1 hour. The solvent was evaporated and the residue dissolved in the minimum volume of methanol and precipitated with ether (yield 83%).

From this molecule it is possible to synthesize cyanine dyes with different substituents at the chloro position. These substituents can introduce new conjugation sites and/or shift the excitation and emission wavelengths to a more useful area of the spectrum. For example, the following dye can be excited by diode lasers at 670 and 780 nm.

Example 9

Synthesis of 2-{7'-[1"-($\epsilon$-carboxypentyl)-3",3"-dimethyl-7"-sulfobenz[e]indolin-2"-ylidene]-3',5'-propane-1'",3'"-diyl)-1',3',5'-heptatrien-1'-yl}-1-($\epsilon$-carboxypentyl)-3 3-dimethyl benz[e] indoleninium-7-sulfonate (10).

To a round-bottomed flask under argon were added 15 ml of anhydrous N,N-dimethylformamide, 300 mg (0.31 mmol) of cyanine dye (9) from Example 9 and 0.5 g (6.1 mmol) of sodium ethanethiolate. The mixture was refluxed for 1 hour and, after cooling, a solid was precipitated with ether (yield 70%).

Example 10

Synthesis of 2-{5'-chloro-7'-[1"-($\gamma$-(N-phthalimidopropyl))-3",3"-dimethyl-7"-sulfobenz[e] indolin-2"-ylidene]-3',5'-(propane-1'"3'"-diyl)-1',3',5'-heptatrien-1'-yl}-1-($\gamma$(N-phthalimidopropyl))-3,3-dimethylbenz[e]indoleninium-7-sulfonate (11).

1-[3'-(N-phthalimidopropyl)]-2,3,3-trimethyl Benz[e] indoleninium-7-sulfonate (330 mg or 773 mmol), (5-phenylamino-2,4-trimethylene-2,4-pentadienylydene) phenylammonium chloride (139 mg or 0.39 mmol) and sodium acetate (76 mg or 0.93 mmol) were dissolved in ethanol (10 ml). After 20 hours of refluxing the solution was evaporated and the residue redissolved in methanol and precipitated with ether (yield 67%).

The purification of the dyes was performed on a Millipore Waters Delta Prep 4000 HPLC unit equipped with a Vydac C18 RP-column, using a gradient elution (for example: $H_2O/CH_3CN$— from 80:20 to 5:95). Because of the numerous ionic sites present in these dyes, to obtain a well-defined composition it was necessary to perform an ion-exchange step by passing an aqueous solution of the dye through a strongly acidic cation-exchanger, such as Dowex 50W in the hydrogen form.

Example 11

General Procedure for the Preparation of Succinimidyl Esters of Carboxyalkyl Sulfo benz[e]indocyanine Dyes.

The following procedure describes the preparation of succinimidyl esters of carboxyalkyl sulfo benz[e] indocyanine dyes. The resulting succinimidyl esters were used as intermediates for labeling biomolecules such as antibodies and antigens.

In a solvent mixture containing anhydrous di-N,N-dimethylformamide (1 ml) and anhydrous pyridine (50 $\mu$l) was dissolved 50 mg of dye containing carboxyalkyl groups (e.g., dyes 7, 8, or 9). Disuccinimidyl carbonate (1.5 equivalents per carboxy group) was added and the mixture was heated at 55 to 60 C for 90 minutes under an atmosphere of argon. The product was isolated by adding ethyl acetate (anhydrous), passing the mixture through a sintered glass filter, and washing the collected product with ethyl acetate. The raw product was dissolved in anhydrous dimethylformamide and was reprecipitated with anhydrous ethyl acetate or ether. The yield was practically quantitative.

Example 12

General Procedure for the Labeling of Protein.

A stock solution of the succinimidyl esters of a carboxyalkyl sulfo benz[e]indocyanine dye was prepared by dissolving 1 mg of active ester in 100 $\mu$l of anhydrous DMF. These solutions were stable for a few days when kept in a dessicator at 4 C. Aqueous solutions of the active esters were stable for a few hours at pH$\leq$7.

One can use aqueous solutions of the active ester-containing dyes in the case where it is not possible to use DMF as a solvent when labeling the protein. One determines the concentration of reactive dye in the stock solution by measuring the absorbance of an aliquot of stock solution properly diluted in phosphate buffer saline, using the color extinction coefficient. In general, the labeling of protein was carried out in carbonate-bicarbonate buffer (0.1M, pH 9.4) for 15 minutes at ambient temperature.

Example 13

Labeling of Anti-$\alpha$-Fetoprotein Monoclonal Antibody.

To one milligram of anti-$\alpha$-fetoprotein monoclonal antibody (MAb anti-AFP) dissolved in 1 ml of carbonate-bicarbonate buffer (0.1 M, pH 9.4) was added with vortex mixing, 20 ml of active ester dye (withdrawn from the stock solution containing 1 mg/100 $\mu$l of active ester dye). The mixture was incubated for 15 minutes at ambient temperature. Dye that did not conjugate with protein was separated from the labeled antibody using gel permeation chromatography on a Sephadex G-25 column (0.7×70 cm) and eluted with phosphate buffer at pH 7. Two colored bands were formed, and the first to elute contained the labeled antibody.

Example 14

Application: Fluorescent Immunoassay (FIA).

As an example of FIA in heterogeneous phase of the sandwich-type, between the analyte to be determined and two monoclonal antibodies specific towards two epitopes different from the analyte, one can make the determination of $\alpha$-fetoprotein in serum. The analytical scheme of the assay is as follows: the first antibody MAb, anti-AFP is used as capture antibody and is conjugated with biotin. The second antibody $Mab_2$ anti-AFP is conjugated with the indicator (for example, Dye 8 with maximum deabsorption at 670 nm.) The immunochemical reaction between the analyte and the monoclonal antibodies takes place in the homogeneous phase, in the presence of a solid phase, for example, plates with wells, sensitized with streptavidin, which constitutes half of the unbound/bound separation.

Schematic of Assay

|−StAV + STET-Mab$_1$anti-AFP + AFP + Mab$_2$anti-AFP-dye

↓

|−StAV + STET-Mab$_1$anti-AFP-AFP-Mab$_2$anti-AFP-dye

↓ incubate 1 h R.T.

|−StAV + STET-Mab$_1$anti-AFP-AFP-Mab$_2$anti-AFP-dye

In the above schematic:

⊢—StA V is the solid phase sensitized with streptavidin;
STET-Mab$_1$anti-AFP is the capture antibody conjugated with biotin;
AFP is α-fetoprotein; and
Mab$_2$anti-AFP-dye is the antibody conjugated with the indicator.

Figure 5:
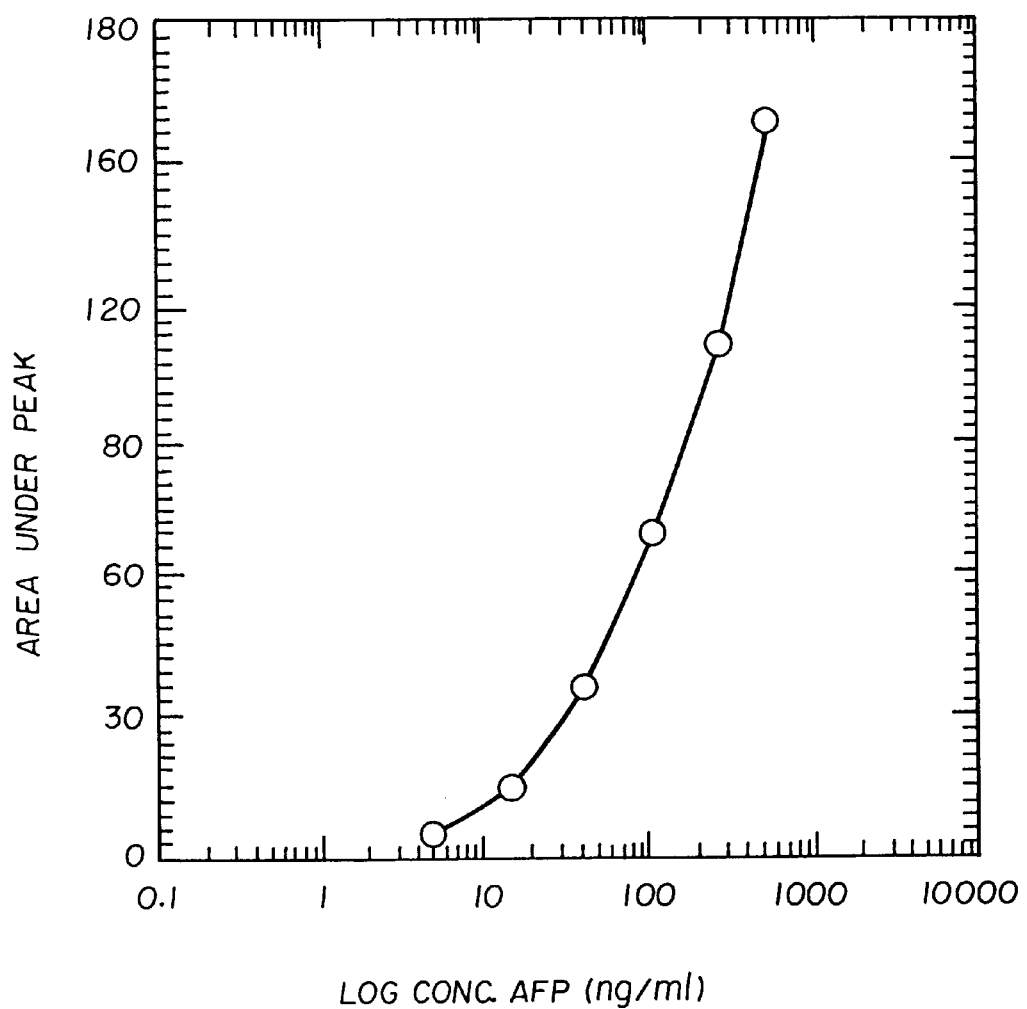
FIG. 5 shows the calibration curve for the determination of α-fetoprotein (AFP).

After washing the plate with an appropriate washing buffer, a number of molecules of Mab$_2$anti-AFP-dye, equal to those of the analyte remain anchored to the solid phase. By means of the construction of a calibration curve (as shown in FIG. 5), one can determine the concentrations of analyte AFP in a withdrawn serum sample. The result can be calculated from the fluorescence light intensity from a constant volume for every sample or reference sample, of a solution of guanidine, by means of which the immunocomplex remains in the solid phase. A typical procedure for this type of determination is as follows:

place in each well 50 μL of sample or reference sample;
100 μL of solution of the STET-Mab$_1$anti-AFP conjugate;
100 μL of the solution of Mab$_2$anti-AFP-dye conjugate;
Incubate for 1 hour at room temperature.
a series of 5 washes with appropriate buffer is carried out automatically using equipment known in the immunochemical art;
place in each well 300 μL of a solution (6 M) of guanidine dichloride;
transfer 300 μL of solution to a cuvette;
subject sample to excitation at 670 nm and the resulting spectral emission is integrated after correction and normalization.

The above description and accompanying drawings are provided for the purpose of describing embodiments of the invention and are not intended to limit the scope of the invention in any way. It will be apparent to those skilled in the art that various modifications and variations can be made in the fluorescent dyes and their uses and in the methods for their synthesis without departing from the spirit or scope of the invention. Thus, it is intended that the present invention cover the modifications and variations of this invention provided they come within the scope of the appended claims and their equivalents.

What is claimed is:

1. A fluorescent compound and its valence tautomers of the formula:

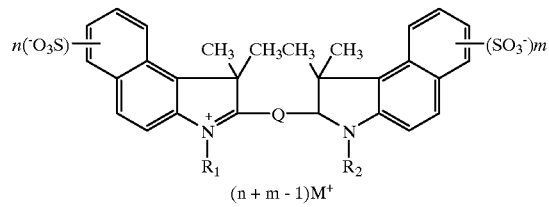

wherein $R_1$ is a functionalized group of the formula —$(CH_2)_j$Y wherein Y is selected from the group consisting of COOH and phthalimido; $R_2$ is a functionalized group of the formula —$(CH_2)_k$Y', wherein Y' is selected from the group consisting of COOH and phthalimido; $M^+$ is a counterion selected from the group consisting of ammonium, alkali metal cations, and alkaline earth metal cations; n=1 to 4; m=1 to 4; j=2 to 10; k=2 to 10; and wherein Q is selected from the group consisting of:

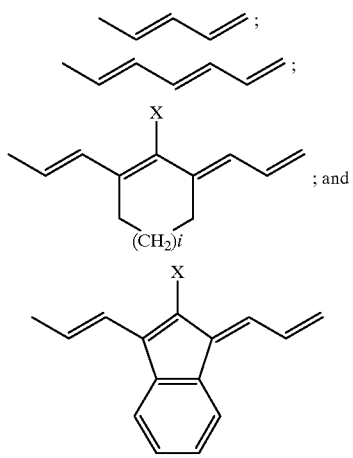

wherein X is selected from the group consisting of hydrogen, F, Cl, Br, I, and substituted aryl, wherein said aryl substituent is selected from the group consisting of SO$_3$H, COOH, NH$_2$, CHO, NCS, epoxy, and COOZ, wherein Z represents a leaving group and i=0 or 1.

2. The fluorescent compound of claim 1 wherein Q is

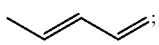

and $R_1$ and $R_2$ are both carboxypentyl.

3. The fluorescent compound of claim 1 wherein Q is

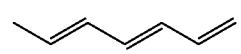

and $R_1$ and $R_2$ are both carboxypentyl.

4. The fluorescent compound of claim 1 wherein Q is

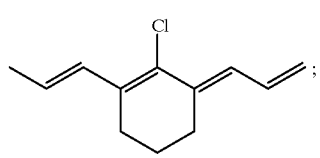

and $R_1$ and $R_2$ are both carboxypentyl.

5. The fluorescent compound of claim 1 wherein Q is
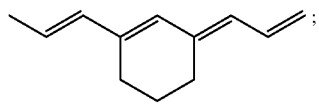
and $R_1$ and $R_2$ are both carboxypentyl.
6. The fluorescent compound of claim 1 wherein Q is
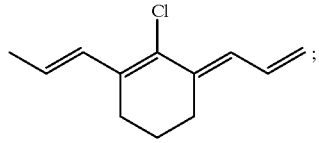
and $R_1$ and $R_2$ are both phthalimidopropyl.
7. A fluorescent compound of claim 1 of the formula:
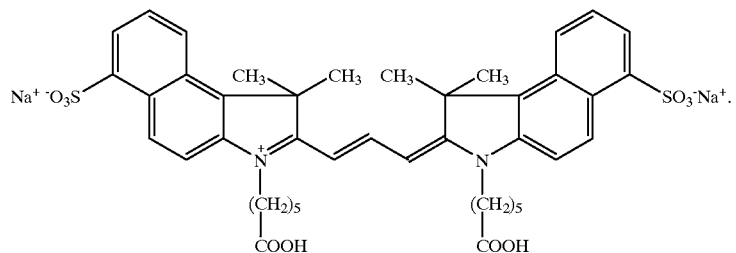
8. A fluorescent compound of claim 1 of the formula:
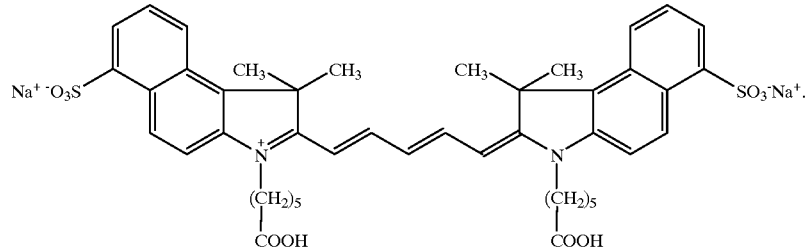
9. A fluorescent compound of claim 1 of the formula:
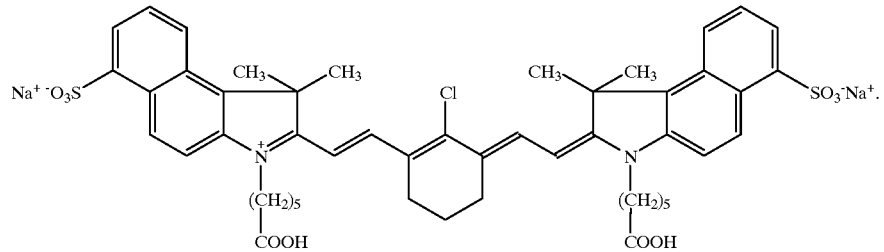

10. A fluorescent compound of claim 1 of the formula:

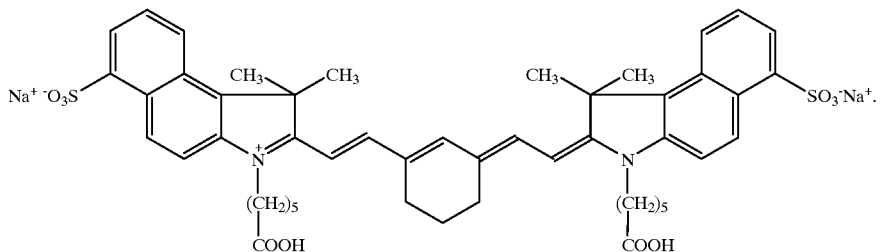

11. A fluorescent compound of claim 1 of the formula:

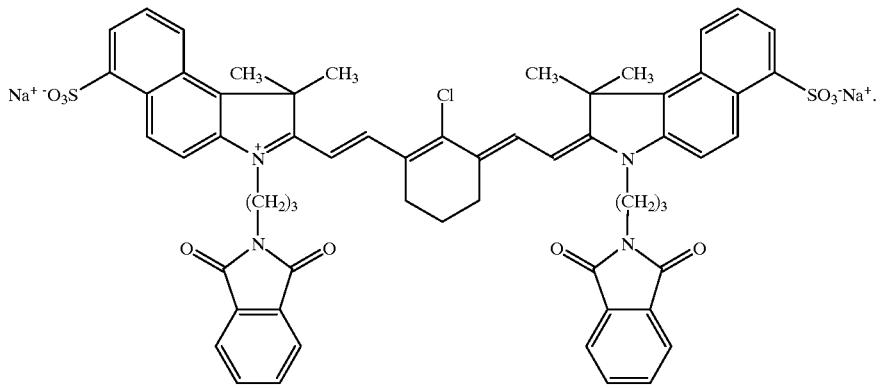

12. A DNA probe labeled with a fluorescent compound of claim 1.

13. A method of assay of an analyte in a sample comprising contacting a DNA probe of claim 12 under suitable conditions for binding with the analyte wherein the binding is representative of the presence or amount of the analyte in the sample and determining the extent of said binding by measuring the fluorescence of the bound DNA probe labeled with said fluorescent compound.

14. The method of assay of claim 13 wherein the analyte is separated from the sample prior to contact with the DNA probe.

15. The method of assay of claim 14 wherein a second DNA probe, which is not labeled, is attached to a solid phase and the analyte is separated from the sample by contact with said second DNA probe under suitable conditions for binding and the remaining sample is removed prior to contact of analyte with the labeled probe.

16. An immunologically binding reagent labeled with a fluorescent compound of claim 1.

17. The binding reagent of claim 16 wherein said reagent is an antibody.

18. The binding reagent of claim 16 wherein said reagent is an antigen.

19. The reagent of claim 17 wherein said antibody is a monoclonal antibody.

20. A method of assay of an analyte in a sample comprising contacting an immunologically binding reagent labeled with a fluorescent compound of claim 1 under suitable conditions for binding with the analyte wherein the binding is representative of the presence or amount of the analyte in the sample and determining the extent of said binding by measuring the fluorescence of the immunologically binding reagent labeled with said fluorescent compound.

21. The method of assay of claim 20 wherein the analyte is separated from the sample prior to contact with the immunologically binding reagent.

22. The method of assay of claim 21 wherein a second immunologically binding reagent, which is not labeled, is attached to a solid phase and the analyte is separated from the sample by contact with said second immunologically binding reagent under suitable conditions for binding and the remaining sample is removed prior to contact of analyte with the labeled immunologically binding reagent.

* * * * *